United States Patent [19]

O'Sullivan et al.

[11] Patent Number: 4,537,858
[45] Date of Patent: Aug. 27, 1985

[54] PLASTATIN

[75] Inventors: Joseph O'Sullivan, Belle Mead; Carol A. Aklonis, North Brunswick; Pushpa Singh, Piscataway, all of N.J.

[73] Assignee: E. R. Squibb & Sons, Inc., Princeton, N.J.

[21] Appl. No.: 623,306

[22] Filed: Jun. 22, 1984

[51] Int. Cl.$^3$ .................. C12P 17/18; C12N 1/20; C07D 311/92
[52] U.S. Cl. .................. 435/119; 435/253; 549/280
[58] Field of Search .............. 435/118, 119, 253; 260/239.3 P; 549/280

[56] References Cited
PUBLICATIONS

Chemical Abstracts, vol. 91, p. 123, Abstract No. 205062x, 1979.
Chemical Abstracts, vol. 88, p. 94, Abstract No. 69634u, 1978.
Fungal Metabolites II by W. B. Turner, Academic Press, Inc., NY, NY, (1983), pp. 115-140, 211.

Primary Examiner—Blondel Hazel
Attorney, Agent, or Firm—Lawrence S. Levinson; Donald J. Barrack

[57] ABSTRACT

Plastatin, an inhibitor of the enzyme phospholipase $A_2$, can be prepared by cultivating *Penicillium chermesinum* under submerged aerobic conditions.

4 Claims, No Drawings

PLASTATIN

SUMMARY OF THE INVENTION

Cultivation of a strain of *Penicillium chermesinum* that has been deposited in the American Type Culture Collection as A.T.C.C. No. 20700, yields a novel chemical substance which has been designated plastatin. Plastatin is an inhibitor of the enzyme phospholipase $A_2$, which initiates the first step in the arachidonic cascade. Plastatin has the structural formula

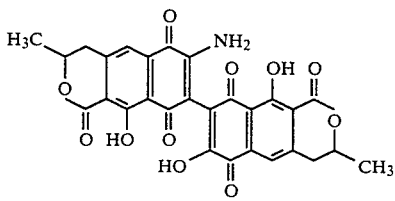

DETAILED DESCRIPTION OF THE INVENTION

The Microorganism

The microorganism used for the production of plastatin is a strain of *Penicillium chermesinum* isolated from the soil. A subculture of the organism may be obtained from the permanent collection of the American Type Culture Collection, Rockville, Maryland. Its accession number in this repository is A.T.C.C. No. 20700. In addition to the specific microorganism described and characterized herein, it should be understood that mutants of the microorganism (e.g., mutants produced through the use of x-rays, ultraviolet radiation or nitrogen mustards) can also be cultivated to produce plastatin.

For isolating and characterizing *Penicillium chermesinum*, a portion of a soil sample in which it is present (one such soil sample was obtained in the Kejimkujik National Park, Nova Scotia, Canada) is air-dried for five days, ground in a mortar with a pestle, and then incubated for two hours in a 60°–65° C. oven. The powdered sample is then plated onto an agar medium having the following composition:

Glycerol—10.0 g
Starch—10.0 g
Sodium glutamate—1.0 g
Sodium nitrate—0.5 g
Proline—0.25 g
Potassium phosphate, dibasic—0.25 g
Magnesium sulfate—0.25 g
Ferrous sulfate—0.01 g
Agar—15.0 g
Distilled water to—1 liter The medium is sterilized and then supplemented with sterile solutions of the following:

1.0% Actidione solution 10 ml/liter
Vitamin solution containing thiamin, hydrochloride, riboflavin, niacin, vitamin $B_6$, inositol, calcium pantothenate and p-aminobenzoic acid, to give a final concentration of 0.05 mg/liter of medium for each vitamin, and biotin to give a final concentration of 0.25 mg/liter of medium.

After incubation for six days at 28° C., isolated colonies of *Penicillium chermesinum* were grown on an agar of the following composition:

Tryptone—5.0 g
Malt extract—3.0 g
Glucose—10.0 g
Yeast extract—3.0 g
Agar—15.0 g
Distilled water to—1 liter The characteristics of *Penicillium chermesinum* A.T.C.C. No. 20700 are:

*Penicillium chermesinum* is a member of the *Penicilium decumbens* series, Section *Monoverticillata*. Colony characteristics after 14 days on Czapeks agar are: the surface is lanate rosaceous; the reverse is light brown with patches of burgundy red.

On Czapeks yeast extract agar: (i) colonies have white centers tinted lightly with pink; (ii) some radial ridging is evident; (iii) the leading edges of the colony is buff to dusty pink colored with accumulations of droplets of clear exudate; (iv) the colony reverse is tan with streaks of reddish brown.

On malt extract agar: (i) sporulation is grayish-green with yellow sections; (ii) the colony reverse is gold to honey-colored.

Microscopic examination shows brush-like monoverticillate conidiophores borne on cottony aerial hyphae. Spores are borne in chains from simple clusters of phialides terminally attached to the conidiophores.

The conidiophores vary considerably in length:
short range from—20–28μ
intermediate range from—43–73μ
long range from—107–112μ

The phialides are about 7.3μ long with a mean diameter of 2.07μ. The conidia are ovoid to spherical, 3.0μ diameter, smooth to finely echinulate.

These characteristics serve to identify the organism producing plastatin as *Penicillium chermesinum*, in agreement with the classification of Thom (Manual of the Penicillin, Raper, K. B. and C. Thom, The Williams and Wilkins Co., Baltimore, 1949).

Production of Plastatin

*Penicillium chermesinum* A.T.C.C. No. 20700 produces plastatin, an inhibitor of the enzyme phospholipase $A_2$, which initiates the first step in the arachidonic cascade. To form plastatin according to the preferred methodology, *Penicillium chermesinum* A.T.C.C. No. 20700 is grown at, or near, room temperature (25° C.) under submerged aerobic conditions in an aqueous nutrient medium containing an assimilable carbohydrate and nitrogen source. The fermentation is carried out until substantial activity is imparted to the medium, usually about 144 to 168 hours, depending upon fermentation conditions.

After the fermentation is completed, the broth is centrifuged to remove the producing organism. Plastatin is extracted from the acidified broth supernate with ethyl acetate and the organic phase is then concentrated in vacuo. After storage of the concentrate at 4° C. for 24 hours, an aqueous layer forms, which is separated from the ethyl acetate layer and extracted with fresh ethyl acetate. The combined ethyl acetate extracts are concentrated to an aqueous slurry in vacuo, adjusted to pH 7, and concentrated to dryness in vacuo. The residue is suspended in a small volume of acetonitrile-water, 1:19, and chromatographed on a column of MCI gel CHP20P*. The active agent is eluted with a linear gradient prepared from acetonitrile-water, 1:19, and 0.01 M hydrochloric acid in acetonitrile-water, 7:3. Further purification is effected by chromatography on cellulose powder with 0.01 M ammonium hydroxide in acetonitrile-water, 10:1. The residue is dissolved in acidified water and extracted with ethyl acetate. The combined ethyl acetate extracts are concentrated in vacuo to dryness.

*MCI gel CHP20P (Mitsubishi Chemical Industries, Ltd., Japan) is a styrene and divinylbenzene copolymer in a bead form having a macroreticular structure.

Utility of Plastatin

Plastatin is useful as an inhibitor of the enzyme phospholipase $A_2$, an enzyme which releases arachidonic acid from membrane phospholipids. Arachidonic acid is converted by the human body to prostaglandins, thromboxanes, prostacyclins and leukotrienes, some of which are involved in pathophysiological processes such as inflammation, dysmenorrhea and immediate hypersensitivity among others. Inhibition of phospholipase $A_2$ controls the flow of such metabolites and is useful in the treatment of arachidonic metabolite related disorders.

Plastatin can be used as a topical antiinflammatory agent to treat skin conditions such as dermatitis, psoriasis, sunburn, eczema, neurodermatitis, or anogenital pruritus, and in inhalation therapy for topical treatment of allergy and asthma.

For the treatment of skin conditions, plastatin may be administered in a conventional pharmaceutical carrier in the form of a cream, ointment, lotion or the like. Plastatin will preferably be used in the range of 0.01 to 5.0% by weight of the vehicle, preferably 0.05 to 2.0% by weight of the vehicle.

For the topical treatment of allergy and asthma, plastatin may be administered in the conventional manner, e.g., as solid medicament which has been atomized. U.S. Pat. Nos. 3,948,164 and 4,147,166 are exemplary of the literature which describes devices that can be used to administer solid medicaments for inhalation therapy.

Plastatin is an acidic substance that forms salts with organic and inorganic bases which are also within the scope of this invention. Such salts include ammonium salts, alkali metal salts such as sodium and potassium, alkaline earth metal salts such as calcium and magnesium, dicyclohexylamine salt, benzathine salt, N-methyl-D-glucamine salt, hydrabamine salt, and salts with amino acids such as lysine and arginine.

The following example further illustrates the preparation of plastatin.

EXAMPLE

Tryptone, malt extract, yeast extract, glucose agar, slants were seeded with *Penicillium chermesinum* A.T.C.C. No. 20700, incubated 21 days at 28° C. and then used to inoculate 100 ml portions of an aqueous medium contained in 30 (500 ml) cotton-plugged Erlenmeyer flasks. The composition of the germination medium was:

Tryptone—5.0 g
Malt extract—3.0
Yeast extract—3.0
Glucose—10.0
Distilled water to—1 liter The medium was sterilized at 121° C. for 15 minutes.

The inoculated germination flasks were incubated for about 48 hours at 25° C. on a rotary shaker, operating at 300 rpm with a 2 inch stroke.

A 10% transfer was made from the germination flasks to 200 Erlenmeyer flasks (500 ml), each Erlenmeyer flask containing 100 ml portions of the same medium as was used for the germination stage. The flasks were incubated at 25° C. for about 144 hours, with the same operating conditions as described for the germinator flasks.

At the end of the incubation period, the contents of the flasks were pooled and the pool filtered to remove the mycelial cake. The filtrate, 17 liters, was acidified to pH 2 with hydrochloric acid, and extracted twice with 10 liter portions of ethyl acetate. The extract was concentrated in vacuo to approximately 1.6 liters, and this concentrate was stored in a cold room (4° C.) for 24 hours. By this time, an aqueous layer had separated from the ethyl acetate concentrate. The aqueous layer was collected and extracted twice with fresh 75 ml portions of ethyl acetate. The ethyl acetate extracts were combined and concentrated to an aqueous slurry in vacuo, adjusted to pH 7 with 1 N sodium hydroxide and concentrated to dryness in vacuo to yield a residue of 6.05 grams. The residue was suspended in acetonitrile-water, 1:19, (3×25 ml) and the resulting suspension was applied to a column of MCI gel CHP20P (75–150µ, 5×36 cm). After washing the column with 1.0 liter of acetonitrile-water, 1:19, elution was carried out with 3.0 liters of a linear gradient of acetonitrile-water, 1:19 and 0.01 M hydrochloric acid in acetonitrile-water, 7:3, collecting 25 ml fractions. The fractions were analyzed by TLC on silica gel, with the lower phase of a solvent composed of chloroform:methanol:water in the ratio of 6:3:1. The active component was detected on the chromatogram as an orange spot ($R_f$=0.27) in visible light and by bioautography.* Fractions 65 through 71 were collected, combined and the pool concentration in vacuo to give 385 mg of residue. This residue was dissolved in 3 ml of 0.01 M ammonium hydroxide in acetonitrile-water (2:1) and chromatographed on a column of Whatman cellulose powder (2.5×25 cm) with 500 ml of a solvent composed of 0.01 M ammonium hydroxide in acetonitrile-water, 10:1. Eight ml fractions were collected. The active fractions were pooled and concentrated in vacuo to give 310 mg of residue. The residue was dissolved in 20 ml of water and 20 ml of 0.02 M hydrochloric acid was added (pH ca. 2); a fine red precipitate formed. The suspension was extracted three times with 50 ml portions of ethyl acetate, keeping most of the precipitate with the ethyl acetate layer. The combined ethyl acetate extracts were concentrated in vacuo to give 172 mg of plastatin as a fine red crystalline material, melting point >300° C.

*Bioautography Reagents and Methodology:
Reagents:
Saline egg yolk solution: 10 egg yolks were thoroughly mixed with 300 ml of 0.85% sterile sodium chloride solution with a magnetic stirrer for 0.5 hours. The mixture was then centrifuged for 5 minutes at 2,000 xg. The supernate was decanted and frozen in 4 ml aliquots at the rate of 1° C. per minute to −90° C. The yolk solutions were then stored at −20° C. pH 7.7 buffer: 1M-$K_2HPO_4$ titrated to pH 7.7 with 1M-$KH_2PO_4$ (ca. 18 ml/100 ml $K_2HPO_4$).
Phospholipase $A_2$ from porcine pancreas (supplied in 3.2 M $(NH_4)_2SO_4$ solution).
Method
To prepare 100 ml agar add 4 ml of saline egg yolk solution, 1 ml of pH 7.7 phosphate buffer and 240 units of enzyme to 95 ml of 0.5% agar. Overlay one 100×15 mm petri dish with 10 ml of egg yolk enzyme agar. Place chromatogram onto agar plate. Allow diffusion for 15 minutes at room temperature and then incubate plate for 1.5 hours at 37° C. An inhibitor of phospholipase $A_2$ will prevent the clearing of the egg yolk suspension in the agar.

Analysis Calc'd. for $C_{28}H_{19}NO_{11}$: C, 61.65; H, 3.51; N, 2.56. Found: C, 61.54; H, 3.77; N, 2.48.

What is claimed is:
1. Plastatin, having the structural formula

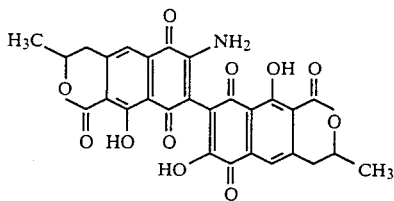

and pharmaceutically acceptable salts thereof.

2. A process for preparing plastatin which comprises cultivating *Penicillium chermesinum* A.T.C.C. No. 20700 in an aqueous nutrient medium containing an assimilable carbohydrate and nitrogen source under submerged aerobic conditions until substantial phospholipase $A_2$ inhibitory activity is imparted to the medium.

3. A process in accordance with claim 2 wherein the organism is cultivated at about 25° C.

4. A biologically pure culture of the microorganism *Penicillium chermesinum* A.T.C.C. No. 20700, said culture being capable of producing plastatin in a recoverable quantity upon fermentation in an aqueous nutrient medium containing an assimilable carbohydrate and nitrogen source.

* * * * *